United States Patent
Ge et al.

(10) Patent No.: US 12,422,443 B2
(45) Date of Patent: Sep. 23, 2025

(54) AMINO-SUBSTITUTED CHROMENOQUINOLINE-BASED FLUORESCENT MARKER, AND PREPARATION AND USE THEREOF

(71) Applicant: SOOCHOW UNIVERSITY, Suzhou (CN)

(72) Inventors: Jianfeng Ge, Suzhou (CN); Mingsen Zhu, Suzhou (CN); Qing Yu, Suzhou (CN); Ru Sun, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 17/928,893

(22) PCT Filed: Dec. 30, 2021

(86) PCT No.: PCT/CN2021/143133
§ 371 (c)(1),
(2) Date: Nov. 30, 2022

(87) PCT Pub. No.: WO2023/092814
PCT Pub. Date: Jun. 1, 2023

(65) Prior Publication Data
US 2024/0353433 A1 Oct. 24, 2024

(30) Foreign Application Priority Data
Nov. 24, 2021 (CN) .................. 202111407628.X (51) Int. Cl.
*G01N 33/92* (2006.01)
*G01N 33/533* (2006.01)
*G01N 33/58* (2006.01)

(52) U.S. Cl.
CPC .......... *G01N 33/92* (2013.01); *G01N 33/533* (2013.01); *G01N 33/582* (2013.01)

(58) Field of Classification Search
USPC .......................................... 436/172
See application file for complete search history.

(56) References Cited

FOREIGN PATENT DOCUMENTS

| CN | 111440143 A | 7/2020 |
|---|---|---|
| CN | 112778258 A | 5/2021 |

OTHER PUBLICATIONS

Weimin Huang, et al., "Development of ratiometric fluorescent pH sensors based on chromenoquinoline derivatives with tunable pKa values for bioimaging" Tetrahedron Letters 55 (2014) 116-119 (Nov. 4, 2013).

(Continued)

*Primary Examiner* — Xiaoyun R Xu
(74) *Attorney, Agent, or Firm* — SZDC Law PC (57) ABSTRACT

The invention provides an amino-substituted chromenoquinoline-based fluorescent marker, and preparation and use thereof. The amino group of an aromatic amine compound is subjected to a one-step cyclization reaction with two o-chloroformylcumarins, to obtain a series of nitrogen-containing heterocyclic compound. Such compounds have excellent fluorescence emission performance, and also have good photostability in various organic solvents. The problem of photostability of cyanine dyes is effectively solved, and these dyes are useful in marking various organelles at cellular level. The introduction of the nitrogen-containing heterocyclic ring improves the biocompatibility of the compound, thus laying a good foundation for use in organisms. Further, the raw materials used in such reactions are cheap and readily available, the steps of synthesizing the marker are simple and easy to operate, and the production cost is effectively reduced while not lowering the performance of the marker. Therefore, the present invention is of commercial value.

8 Claims, 4 Drawing Sheets

(56) References Cited

OTHER PUBLICATIONS

Santosh Kumari, et al., "NH4OAc-promoted Cascade Approach towards Aberrant Synthesis of Chromene-fused Quinolinones" European Journal of Organic Chemistry, pp. 705-714, Dec. 31, 2019.

Dieter Heber, "Zur Synthese von 6-Oxo-6H-[1]enzopyrano[4,3-b]chinolinen" Arch. Pharm. Vol. 320, pp. 595-599 (Dec. 31, 1987).

Hashem Sharghi et al., "Synthesis of chromeno[3,4-b]quinoline derivatives by heterogeneous [Cu(II)BHPPDAH] catalyst without being immobilized on any support under mild conditions using PEG 300 as green solvent" Mol Divers (2013) 17:721-730 (Aug. 22, 2013).

Sunita Joshia, "Synthesis, solvatochromism and electric dipole moment study of coumarin-fused quinoline: experimental and quantum chemical computational investigations" Eur. Phys. J. D (2021) 75:153 (May 11, 2021).

AMINO-SUBSTITUTED CHROMENOQUINOLINE-BASED FLUORESCENT MARKER, AND PREPARATION AND USE THEREOF

This application is the National Stage Application of PCT/CN2021/143133, filed on Dec. 30, 2021, which claims priority to Chinese Patent Application No. 202111407628.X, filed on Nov. 24, 2021, which is incorporated by reference for all purposes as if fully set forth herein.

FIELD OF THE INVENTION

The present invention relates to the field of fluorescence labeling technology, and specifically to an amino-substituted chromenoquinoline-based fluorescent marker, and preparation and use thereof.

DESCRIPTION OF THE RELATED ART

Lipid droplet, as a dynamic independent organelle, is an important site for the storage of neutral lipids in the nucleus, and promotes the absorption metabolism, transport and signal transmission of lipids in cells in the regulation of lipids, to maintain the smooth progress of various physiological activities (see J.-W. Shi, Y. Tian, X.-L. Zhang, et al., An AIEgen-Based Fluorescent Probe for Highly Selective and Specific Imaging of Lipid Droplets in L02 and HepG2 Cells, Sensors and Actuators B: Chemical, 2019 (284) 545-552). Mitochondrion consists of a double-membrane system, and is an organelle involved in energy metabolism and intracellular homeostasis in eukaryotic cells. Therefore, it acts as a power source for energy exchange, metabolic factory and information transmission center in the activities in the entire organism, and is a center of cell metabolism (see X.-Y. Li, Y.-M. Hu, H.-M. Ma, et al., Mitochondria-Immobilized Near-Infrared Ratiometric Fluorescent pH Probe to Evaluate Cellular Mitophagy, Anal Chem, 2019 (91) 11409-11416). In a complex cellular environment, it is extremely important to observe and detect the state of lipid droplets and mitochondria (see D. I. Danylchuk, P. H. Jouard, A. S. Klymchenko, Targeted Solvatochromic Fluorescent Probes for Imaging Lipid Order in Organelles under Oxidative and Mechanical Stress, J. Am. Chem. Soc, 2021 (143) 912-924). Among the currently available detection methods, fluorescent labeling is widely used by researchers due to the good selectivity, high sensitivity, and convenience in operation. In recent years, more and more dye-based fluorescent probes for labeling lipid droplets and mitochondria become available (see (1) J.-Y. Ni, R. Sun, J.-F. Ge, et al., Convenient Construction of Fluorescent Markers for Lipid Droplets with 1,8-Naphthalimide Unit, Dyes and Pigments, 2021 (186) 109003. (2) W. Ma, B. Xu, Y.-J. Xu, et al., The Application of Amide Units in the Construction of Neutral Functional Dyes for Mitochondrial Staining, J. Mater. Chem. B, 2021 (9) 2524).

During the long-term and repeated use of currently commonly used commercial markers for organelles, some shortcomings gradually become notorious. Nile Red and BODIPY derivatives are commonly used commercial markers for lipid droplets. However, the Nile Red derivative is non-specific for lipid droplets during the labeling process, and other organelles may also be stained in some cases. The use of the BODIPY derivative is also limited due to the small Stokes shift. During the process of labeling mitochondria, the commonly used commercial markers are mostly salts, for example, a triphenylphosphonium salt, a pyridium salt, an indolium salt, and others. Although they can be localized to mitochondria, some problems are present. When these cations enter the cells, they will change the membrane potential of mitochondria and thus change the microenvironment in the cells, affecting the physiological activities of living organisms (see Y. Wang, B. Xu, R. Sun, J.-F. Ge, et al., The Application of Nitrogen Heterocycles in Mitochondrial-Targeting Fluorescent Markers with Neutral Skeletons, J. Mater. Chem. B, 2020 (8) 7466).

SUMMARY OF THE INVENTION

To solve the above problems, a series of chromenoquinoline-based heterocyclic compounds are obtained in the present invention by a one-step reaction of an aromatic amine with a coumarin derivative by controlling the feed ratio. These compounds are useful in the imaging of lipid droplets or mitochondria in biological use.

The present invention provides an amino-substituted chromenoquinoline-based fluorescent marker, having one or more chromenoquinoline rings at the structural center, and one or more dialkylamino groups is attached to the chromenoquinoline ring.

Preferably, the amino-substituted chromenoquinoline-based fluorescent marker has a structural formula as shown by any one of Formulas 1a-1d:

Preferably, 1-2 benzene rings are linked to the chromenoquinoline ring in the amino-substituted chromenoquinoline-based fluorescent marker.

Preferably, the amino-substituted chromenoquinoline-based fluorescent marker is synthesized by reacting an aromatic amine and a coumarin fluorescent precursor.

More preferably, the aromatic amine is 1-naphthylamine (5a), N,N-diethylp-phenylenediamine (5b) or p-phenylenediamine (5c).

More preferably, the coumarin fluorescent precursor is 4-chloro-3-formylcoumarin (5d) or 4-chloro-7-(diethylamino)-2-oxo-2H-chromene-3-carbaldehyde (5e).

Preferably, the molar ratio of the aromatic amine to the coumarin fluorescent precursor is 1:1-2.

Preferably, the aromatic amine is reacted with the coumarin fluorescent precursor in the presence of a catalyst to synthesize the amino-substituted chromenoquinoline-based fluorescent marker, in which the catalyst is a Lewis acid.

More preferably, the Lewis acid is aluminum trichloride, boron trifluoride, sulfur trioxide or ferric bromide.

Preferably, the reaction solvent is tetrahydrofuran; and the molar ratio of the aromatic amine to the catalyst is 1:1-2.

The present invention further provides use of the amino-substituted chromenoquinoline-based fluorescent marker as a fluorescent marker for an organelle.

Preferably, the amino-substituted chromenoquinoline-based fluorescent markers 1a, 1b and 1c are used for the imaging of lipid droplets; and the amino-substituted chromenoquinoline-based fluorescent marker 1d is used for the imaging of mitochondria.

Compared with the prior art, the technical solution of the present invention has the following advantages:

The present invention discloses a series of novel heterocyclic fluorescent markers for the first time. The introduction of a nitrogen containing heterocyclic ring improves the biocompatibility of the compound to promote the use in the biological field. Moreover, the reaction process of the aromatic amine and the coumarin derivative is convenient and fast, and requires only a one-step operation to afford the target product, which can be localized to lipid droplets or mitochondria, and thus has biological application value.

The nitrogen-containing heterocyclic ring acts as the center of such a structure, and improves the biocompatibility. N,N-diethylamino is a commonly used strong electron donating group located at both ends of the structure, which affects the optical performance of the compound while improving the solubility in an organic solvent.

A fluorescent marker that can be localized to lipid droplets or mitochondria are synthesized by cyclization of an inexpensive and readily available aromatic amine with a typical coumarin derivative. Such a fluorescent marker can not only maintain the excellent fluorescence performance of coumarin, but also finally convert the coumarin derivative without targeting ability into a fluorescent probe that can target lipid droplets or mitochondria through modification of the structure. More importantly, the whole process of the reaction with two cheap and readily available raw materials is simple, convenient and fast.

In the present invention, a cheap and readily available aromatic amine compound is used and the tetrahydrofuran aprotic solvent is used as the organic solvent for the reaction. In the reaction, anhydrous aluminum trichloride are involved, to ensure the smooth progress of the reaction. Therefore, the method has practical application value.

After the heterocyclic fluorescent probes of the present invention are co-incubated with Hela cells, respectively, fluorescence imaging of lipid droplets or mitochondria can be achieved. Such fluorescent markers have low cytotoxicity and little damage to biological samples during cell imaging, and have large Stokes shift and low background interference. Therefore, the present invention is of great scientific significance and commercial value.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

In the following examples, the cells are imaged by laser confocal microscopy, where excitation at 405 nm is employed in the green light channel, and the fluorescence signal in the range of 468-550 nm is collected; and excitation at 561 nm is employed in the red light channel, and the fluorescence signal in the range of 570-750 nm is collected.

Figure 1:
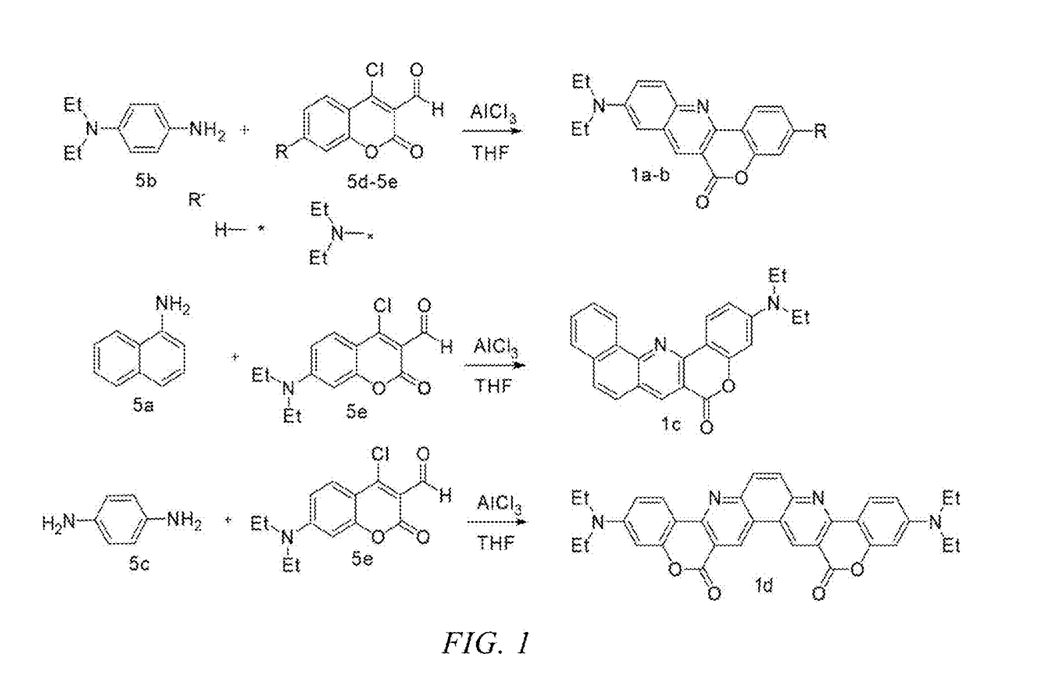
FIG. 1 shows the synthetic routes for the fluorescent markers 1a-1d involved in the present invention.

The synthetic routes in the examples of the present invention are shown in FIG. 1, in which 5a-5e represent the numbers of different raw materials. In the synthesis of the compound of the present invention, the ratios of raw materials and the purification methods are conventional ratios or conventional purification methods. The examples are schematic representations, and the correctness of the product structure is verified by proton nuclear magnetic resonance spectroscopy, carbon-13 nuclear magnetic resonance spectroscopy and high-resolution mass spectrometry in the present invention.

Example 1

The steps for the synthesis of dye 1a were as follows:
The compound N,N-diethylp-phenylenediamine 5b (1.0 mmol, 393.0 mg), Compound 5d (1.0 mmol, 500.0 mg) and aluminum trichloride (1.0 mmol, 319.0 mg) were dissolved in tetrahydrofuran (20.0 ml), and refluxed for 3 to 4 hrs, during which the progress of the reaction was detected by TLC. After cooling to room temperature, the solvent was removed directly by rotary evaporation, and after separation by column chromatography (eluent: pure dichloromethane), pure dye 1a as an orange solid was obtained (175.3 mg, yield 44.5%). 1H NMR (300 MHz, DMSO-$d_6$) δ (ppm) 8.97 (s, 1H, Ar—H), 8.57 (s, 1H, Ar—H), 8.58 (d, J=5.7 Hz, 1H, Ar—H), 8.02 (d, J=9.6 Hz, Ar—H), 7.68 (d, J=8.1 Hz, 1H, Ar—H), 7.56 (t, J=14.4 Hz, 1H, Ar—H), 7.42 (d, J=8.7 Hz, 2H, Ar—H), δ 7.20 (s, 1H, Ar—H), 3.53 (q, J=6.0 Hz, 4H, 2×$CH_2$), 2.50 (s, 6H, 2×$CH_3$). $^{13}$C NMR (151 MHz, CDCl$_3$) δ (ppm) 161.9, 151.9, 144.9, 137.4, 130.8, 130.2, 123.1, 117.1, 115.8, 103.8, 44.7, 12.4. HRMS (ESI$^+$) m/z calculated for $C_{20}H_{18}N_2O_2^+$, [M+Na]$^+$: 341.1260, found: 341.1223.

Example 2

The steps for the synthesis of dye 1b were as follows:
The compound N,N-diethylp-phenylenediamine 5b (1.0 mmol, 176.16 mg), Compound 5e (1.0 mmol, 300.0 mg) and aluminum trichloride (1.0 mmol, 142.9 mg) were dissolved in tetrahydrofuran (20.0 ml), and refluxed for 3 to 4 hrs, during which the progress of the reaction was detected by TLC. After cooling to room temperature, the solvent was removed directly by rotary evaporation, and after separation by column chromatography (eluent: pure dichloromethane), pure dye 1b as an orange red solid was obtained (66.8 mg, yield 23%). 1H NMR (300 MHZ, DMSO-$d_6$) δ (ppm) 8.87 (s, 1H, Ar—H), 8.29 (d, J=6.6 Hz, 1H, Ar—H), 7.91 (d, J=7.2 Hz, 1H, Ar—H), 7.60 (d, J=6.6 Hz, Ar—H), 7.13 (s, 1H, Ar—H), 6.77 (t, J=6.6 Hz, 1H, Ar—H), 6.56 (s, 1H, Ar—H), 3.46 (q, J=18 Hz, 8H, 4×$CH_2$), 1.17 (q, J=6.0 Hz, 12H, 4×$CH_3$). $^{13}$C NMR (151 MHz, CDCl$_3$) δ (ppm) 162.7, 153.9, 145.5, 137.9, 129.5, 128.3, 125.4, 123.0, 114.8, 108.9, 104.6, 98.1, 44.7, 12.6. HRMS (ESI$^+$) m/z calculated for $C_{24}H_{27}N_3O_2^+$, [M+H]$^+$: 390.2176, found: 390.2217.

Example 3

The steps for the synthesis of dye 1c were as follows:
The compound 1-naphthylamine 5a (1.0 mmol, 153.6 mg), Compound 5e (1.0 mmol, 300 mg) and aluminum trichloride (1.0 mmol, 142.9 mg) were dissolved in tetrahydrofuran (20.0 ml), and refluxed for 3 to 4 hrs, during which the progress of the reaction was detected by TLC. After cooling to room temperature, the solvent was removed directly by rotary evaporation, and after separation by column chromatography (eluent: pure dichloromethane), pure dye 1c as a bright yellow solid was obtained (123.7 mg, yield 41.2%). 1H NMR (300 MHz, DMSO-$d_6$) δ (ppm) 9.33 (d, J=5.4 Hz, 1H, Ar—H), 9.01 (s, 1H, Ar—H), 8.53 (d, J=6.9 Hz, 1H, Ar—H), 8.04 (d, J=5.4 Hz, 1H, Ar—H), 7.98 (d, J=6.6 Hz, 1H, Ar—H), 7.84 (q, J=9.0 Hz, 3H, Ar—H), 6.83 (d, J=6.3 Hz, 1H, Ar—H), 6.56 (s, 1H, Ar—H), 3.46 (q, J=5.1 Hz, 4H, 2×$CH_2$), 1.16 (q, J=9.9 Hz, 6H, 2×$CH_3$). $^{13}$C NMR (151 MHz, CDCl$_3$) δ (ppm) 162.3, 154.7, 150.5, 149.8, 138.9, 135.1, 130.8, 129.7, 127.8, 127.0, 126.1, 125.6, 124.4, 109.1, 98.1, 45.1, 12.5. HRMS (ESI$^+$) m/z calculated for $C_{24}H_{20}N_2O_2^+$, [M+Na]$^+$: 391.1417, found: 391.1433.

Example 4

To verify that cyclization can occur at symmetric positions at two sides of the benzene ring, dye 1d was further synthesized with the compound p-phenylenediamine 5c.
The steps for the synthesis of dye 1d were generally as follows:
The compound p-phenylenediamine 5c (1.0 mmol, 55.09 mg), Compound 5e (2.0 mmol, 285.0 mg) and aluminum trichloride (2.0 mmol, 135.8 mg) were dissolved in tetrahydrofuran (25.0 ml), and refluxed for 6 to 7 hrs, during which the progress of the reaction was detected by TLC. After cooling to room temperature, the solvent was removed directly by rotary evaporation, and after separation by column chromatography (eluent: dichloromethane/methanol (40/1 V/v)), pure dye 1d as an orange yellow solid was obtained (108.73 mg, yield 21.8%). $^1$H NMR (300 MHZ, CDCl$_3$-$d_6$) δ (ppm) 7.94 (d, J=9.0 Hz, 1H, Ar—H), 7.86 (d, J=9.0, 1H, Ar—H), 6.88 (s, 2H, Ar—H), 6.75 (d, J=7.8 Hz, 2H, Ar—H), 6.59 (d, J=8.7, 2H, Ar—H), 6.37 (s, 2H, Ar—H), 3.44 (m, 8H, 4×$CH_2$), 1.20 (t, J=14.1 Hz, 12H, 4×$CH_3$). HRMS (ESI$^+$) m/z calculated for $C_{24}H_{20}N_2O_2^+$, [M+H]$^+$: 559.2340, found: 559.4016.

Effect Comparison Example 1

Figure 2:
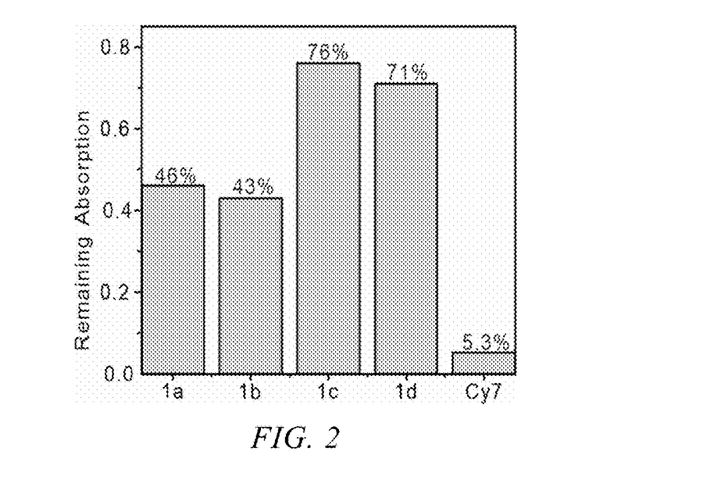
FIG. 2 shows the photostability of the fluorescent markers 1a-1d.

The photostability of the above prepared dyes 1a-1d was tested (at a concentration of 10 μM). Dyes 1a-1d and the reference substance Cy7 of corresponding weights were weighed, and respectively dissolved in acetonitrile (at a concentration of 10 μM). All samples were irradiated with a Philips iodine-tungsten lamp (500 W), where the distance between the lamp and the sample was set to 25 cm. An 8 cm-thick sodium nitrite (60 g per liter) cold trap was placed between the lamp and the sample, to eliminate the heat and short-wavelength light. The irradiation was continued for 6 hrs, during which UV and fluorescence were performed every half hour. After six hours, the light stability was measured by residual absorptivity calculated based on the change in the absorption intensity at various times before and after the irradiation. As shown in FIG. 2, the photostability of the fluorescent markers is respectively 1a: 46%, 1b: 43%, 1c: 76%, 1d: 71%, and Cy7: 5.3%. It can be seen that dyes 1a-1d have higher photostability compared to cyanine dyes.

Effect Comparison Example 2

Figure 3:
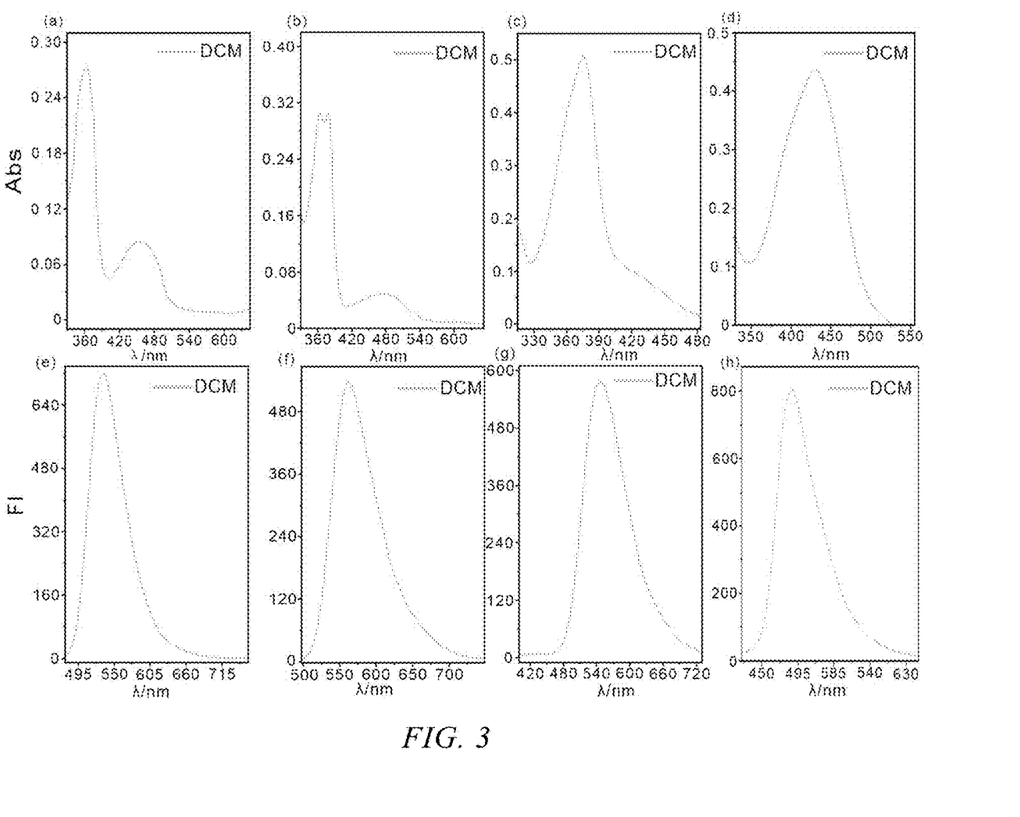
FIG. 3 shows the UV-Vis absorption and fluorescence spectra of the fluorescent markers 1a-1d in chloroform.

The ultraviolet absorption and fluorescence emission performances of the dyes 1a-1d prepared above (at a concentration of 10 μM) in dichloromethane were tested. The horizontal ordinate is the wavelength, and the vertical ordinate is the absorbance and fluorescence intensity, respectively. The results are shown in FIG. 3.
The ultraviolet absorption and fluorescence emission spectra of the fluorescent marker 1a (at a concentration of 10 μM) in dichloromethane are shown in FIG. 3. The fluorescent marker 1a has the maximum absorption at 452 nm (FIG.

3 (*a*)); and the fluorescent marker 1a has the highest fluorescence intensity at 532 nm (FIG. 3 (*e*)), where the excitation wavelength is 428 nm, and the slit width is 3 nm/3 nm.

The ultraviolet absorption and fluorescence emission spectra of the fluorescent marker 1b (at a concentration of 10 μM) in dichloromethane are shown in FIG. 3. The fluorescent marker 1b has the maximum absorption at 473 nm (FIG. 3 (*b*)); and the fluorescent marker 1b has the highest fluorescence intensity at 562 nm (FIG. 3 (*f*)), where the excitation wavelength is 407 nm, and the slit width is 3 nm/3 nm.

The ultraviolet absorption and fluorescence emission spectra of the fluorescent marker 1c (at a concentration of 10 μM) in dichloromethane are shown in FIG. 3. The fluorescent marker 1c has the maximum absorption at 375 nm (FIG. 3 (*c*)); and the fluorescent marker 1c has the highest fluorescence intensity at 546 nm (FIG. 3 (*g*)), where the excitation wavelength is 461 nm, and the slit width is 3 nm/3 nm.

The ultraviolet absorption and fluorescence emission spectra of the fluorescent marker 1d (at a concentration of 10 μM) in dichloromethane are shown in FIG. 3. The fluorescent marker 1d has the maximum absorption at 429 nm (FIG. 3 (*d*)); and the fluorescent marker 1d has the highest fluorescence intensity at 495 nm (FIG. 3 (*h*)), where the excitation wavelength is 430 nm, and the slit width is 5 nm/3 nm.

Effect Comparison Example 3

Figure 4:
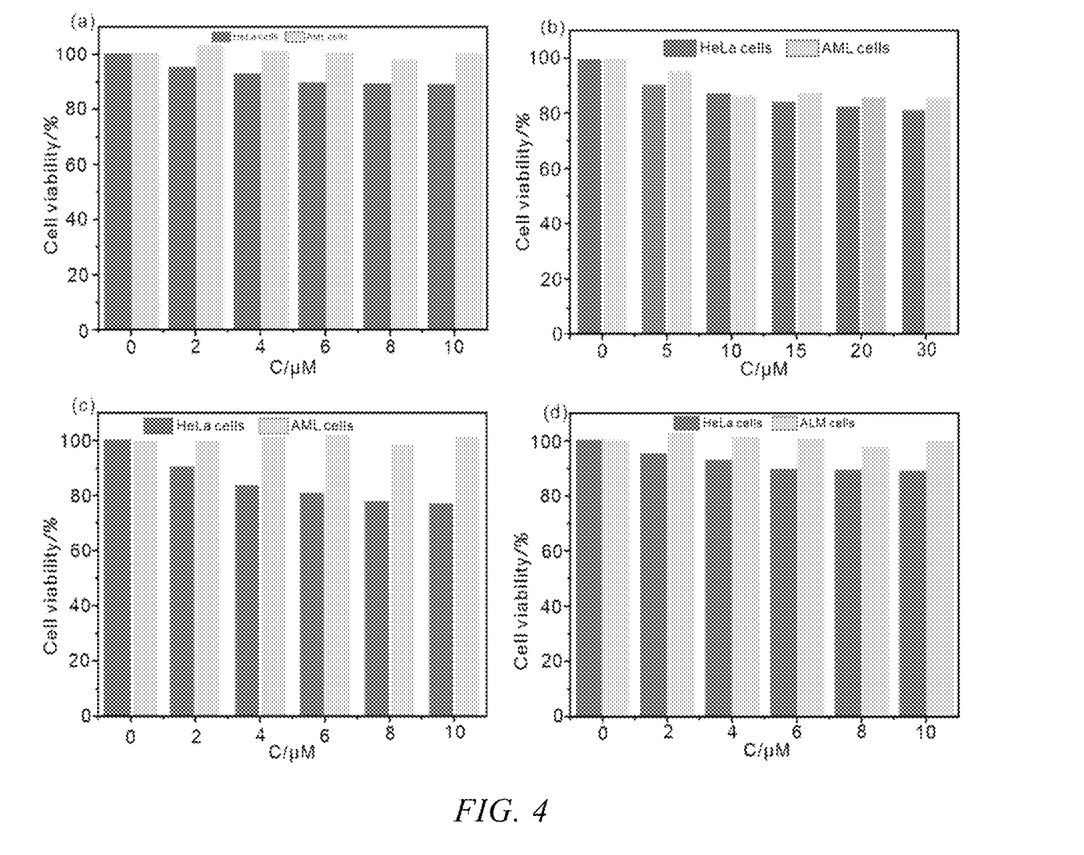
FIG. 4 shows the cytotoxicity test results of the fluorescent markers 1a-1d.

Moreover, the cytotoxicity of the fluorescent markers 1a-1d was also tested in the present invention. The viability of Hela cells in the presence of these dyes was measured by the CCK-8 method. The Hela cells were incubated with various concentrations of dyes (2 4, 6, 8 and 10 μM) for 6 hrs. As shown in FIG. 4. the cytotoxicity test results of fluorescent markers 1a-1d show that they have good cell viability and are suitable for live cell imaging.

In FIG. 4, Cell survival rate (%)=$(A_{sample}-A_b)/(A_c-A_b)$, where $A_c$: negative control (including the medium and the cells, without the test dye), $A_b$: blank ((including the test dye and the medium, without the cells), $A_{sample}$: test group (including the medium, the cells and the test dye).

Effect Comparison Example 4

Figure 5:
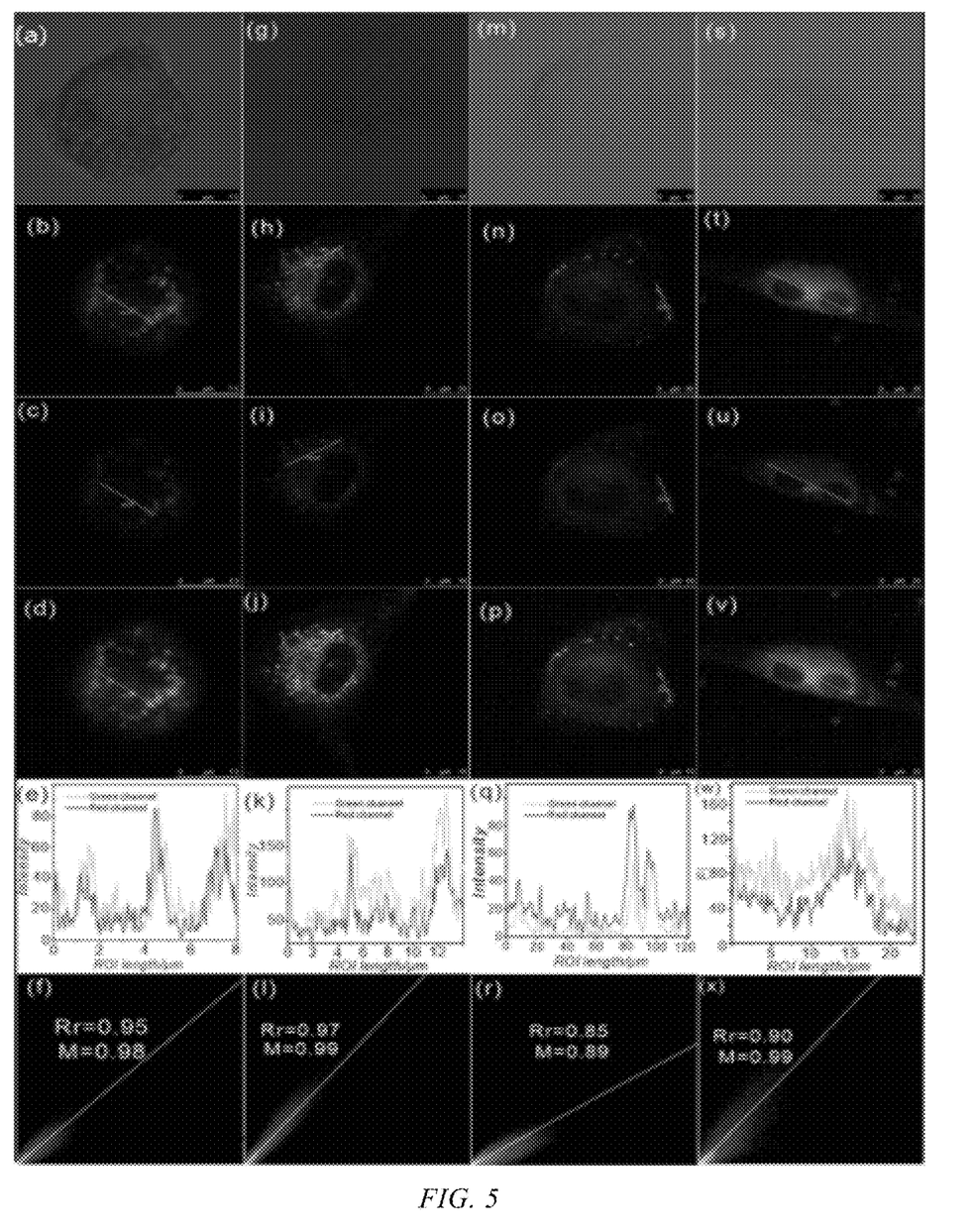
FIG. 5 shows cell images imaged with the fluorescent markers 1a-1d in HeLa cells.

To test the fluorescent labeling ability of the fluorescent marker 1a compared with a commercial lipid droplet marker, the fluorescent marker 1a was prepared into a stock solution in dimethyl sulfoxide, and then added to a conventional cell culture medium, to give a concentration of the fluorescent marker 1a in the cell culture medium of 6 μM. Subsequently, Nile Red (100 nM), a lipid droplet red marker, was added and co-incubated with Hela cells in an incubator at saturated humidity, 37° C., and 5% $CO_2$ for 5 min (the same below); The cells were washed three times with a PBS buffer, and imaged by laser confocal microscopy, where excitation at 405 nm was employed in the green light channel, and the fluorescence signal in the range of 468-550 nm was collected; and excitation at 561 nm was employed in the red light channel, and the fluorescence signal in the range of 570-750 nm was collected. The results are shown in FIG. 5, in which (a) is the bright field, (b) is the cell image with the fluorescent marker 1a, (c) is the cell image with the lipid droplet Red marker, (d) is overlapped image of the green light channel and the red light channel, (e) is the fluorescence intensity of the ROI line in the overlapped image, and (f) is the colocalization assay, where the colocalization coefficient is 0.95. The results show that the fluorescent image with the fluorescent marker 1a and the fluorescent image with the commercial mitochondrial red marker Nile Red have consistent distribution in cells, and comparable intensity, showing that the fluorescent marker 1a has lipid droplet labeling ability in Hela cells, and can be used as a green marker for lipid droplets.

Effect Comparison Example 5

To verify the labeling effect of the fluorescent marker 1b (6 μM) on lipid droplets in Hela cells, the same experimental method as that with the fluorescent marker 1a was used. As shown in FIG. 5, (g) is the bright field, (h) is the cell image with the fluorescent marker 1b, (i) is the cell image with the lipid droplet Red marker, (j) is overlapped image of the green light channel and the red light channel, (k) is the fluorescence intensity of the ROI line in the overlapped image, and (l) is the colocalization assay, where the colocalization coefficient is 0.97. The results show that similar to the probe 1a, the fluorescent marker 1b also has good targeting ability to lipid droplets in Hela cells.

Effect Comparison Example 6

The experimental method with the fluorescent marker 1c (5 μM) was the same as that with the fluorescent marker 1a. As shown in FIG. 5, (m) is the bright field, (n) is the cell image with the fluorescent marker 1b, (o) is the cell image with the lipid droplet Red marker, (p) is overlapped image of the green light channel and the red light channel, (q) is the fluorescence intensity of the ROI line in the overlapped image, and (r) is the colocalization assay, where the colocalization coefficient is 0.85. The results show that similar to the probes 1a and 1b, the fluorescent marker 1c also has good targeting ability to lipid droplets in Hela cells.

Effect Comparison Example 7

To verify whether Compound 1d can be used in fluorescence imaging of lipid droplets in Hela cells just as the probes 1a-1c do, a cell assay was carried out. The fluorescent marker 1d was prepared into a stock solution in dimethyl sulfoxide, and then added to a conventional cell culture medium, to give a concentration of the fluorescent marker 1d in the cell culture medium of 8 μM. The Hela cells were co-incubated in an incubator at saturated humidity, 37° C., 5% $CO_2$ for 5 min. The cells were washed three times with a PBS buffer, and imaged by laser confocal microscopy, where excitation at 405 nm was employed in the green light channel, and the fluorescence signal in the range of 468-550 nm was collected. The results show that 1d does not stain the lipid droplets in the cells, and the staining site is probably mitochondria. To verify this result, colocalized cell imaging was performed again, the commercial red marker of mitochondria, CMA Ros (100 nM) was added to the previous cell culture medium. The results are shown in FIG. 5, in which(s) is the bright field, (t) is the cell image with the fluorescent marker 1d, (u) is the cell image with the lipid droplet Red marker, (v) is overlapped image of the green light channel and the red light channel, (w) is the fluorescence intensity of the ROI line in the overlapped image, and (x) is the colocalization assay, where the colocalization coefficient is 0.90. The result indicates that dye 1d has the ability to label mitochondria, and can be used as a green marker for mitochondria.

It can be seen that the present invention discloses, for the first time, a series of amino-substituted chromenoquinoline fluorescent markers synthesized by the cyclization reaction of an aromatic amine and a coumarin derivative, with which fluorescence imaging of lipid droplets or mitochondria can be achieved. In the present invention, the compounds have extremely strong fluorescence intensity in the organic solvent dichloromethane after a one-step cyclization reaction, and has high optical stability compared with cyanine dyes. Moreover, the compound have low cytotoxicity, little damage to biological samples, and high selectivity when further used in biological cell imaging, and can rapidly stain and image cells. The imaging results indicate that such compounds can specifically target lipid droplets or mitochondrial organelles.

Obviously, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. An amino-substituted chromenoquinoline-based fluorescent marker, having a structural formula selected from the group consisting of

1a

1b

1c

1d

2. The amino-substituted chromenoquinoline-based fluorescent marker according to claim 1, wherein the fluorescent marker is synthesized by reacting an aromatic amine and a coumarin fluorescent precursor.

3. The amino-substituted chromenoquinoline-based fluorescent marker according to claim 2, wherein the aromatic amine is 1-naphthylamine, N,N-diethylp-phenylenediamine or p-phenylenediamine.

4. The amino-substituted chromenoquinoline-based fluorescent marker according to claim 2, wherein the coumarin fluorescent precursor is 4-chloro-3-formylcoumarin or 4-chloro-7-(diethylamino)-2-oxo-2H-chromene-3-carbaldehyde4-chloro-7-(diethylamino)-2-oxo-2H-chromene-3-carbaldehyde.

5. The amino-substituted chromenoquinoline-based fluorescent marker according to claim 2, wherein the molar ratio of the aromatic amine to the coumarin fluorescent precursor is 1:1-2.

6. The amino-substituted chromenoquinoline-based fluorescent marker according to claim 2, wherein the aromatic amine is reacted with the coumarin fluorescent precursor in the presence of a catalyst to synthesize the amino-substituted chromenoquinoline-based fluorescent marker, in which the catalyst is a Lewis acid.

7. The amino-substituted chromenoquinoline-based fluorescent marker according to claim 6, wherein the molar ratio of the aromatic amine to the catalyst 1:1-2.

8. Use of the amino-substituted chromenoquinoline-based fluorescent marker according to claim 1.

* * * * *